United States Patent
Kadobayashi

(10) Patent No.: US 8,197,254 B2
(45) Date of Patent: Jun. 12, 2012

(54) SET OF ARTIFICIAL TEETH HAVING CONVEX ADJUSTMENT SURFACE

(75) Inventor: Yusei Kadobayashi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 12/707,110

(22) Filed: Feb. 17, 2010

(65) Prior Publication Data

US 2011/0039231 A1 Feb. 17, 2011

(30) Foreign Application Priority Data

Aug. 11, 2009 (JP) ................... 2009-186459

(51) Int. Cl.
*A61C 13/00* (2006.01)
(52) U.S. Cl. ........................................ 433/171
(58) Field of Classification Search .......... 433/167–172, 433/181–183, 186, 196–198
See application file for complete search history.

(56) References Cited

U.S. PATENT DOCUMENTS 2,598,769 A 6/1952 Donavan
3,947,963 A * 4/1976 Haker ........................... 433/197

FOREIGN PATENT DOCUMENTS

| JP | 63-275337 | 11/1988 |
| JP | 8-280713 | 10/1996 |
| JP | 9-285475 | 11/1997 |
| JP | 2002-177301 | 6/2002 |

OTHER PUBLICATIONS

Notice of Reason for Rejection (in English language) issued Mar. 9, 2010 in corresponding Japanese Patent Application No. 2009-186459.

* cited by examiner

*Primary Examiner* — Sunil K Singh
(74) *Attorney, Agent, or Firm* — Wenderoth, Lind & Ponack, L.L.P.

(57) ABSTRACT

A set of artificial teeth allows for easy occlusion adjustment without high precision in arrangement. One of a pair of occluding upper and lower artificial molar teeth has convex adjustment surfaces which are formed of a spherical surface, a cylindrical surface or a conical surface on an occlusal surface thereof, and the other of the pair of artificial molar teeth has opposing surfaces which are formed of a flat surface, a spherical surface, a cylindrical surface or a conical surface in point contact or line contact with the adjustment surfaces on an occlusal surface thereof.

4 Claims, 5 Drawing Sheets

FIG. 7

|  | SHAPE OF ADJUSTEMT SURFACE ||||
|---|---|---|---|---|
|  | SPHERICAL | CYLINDRICAL | CONICAL | FLAT |
| SHAPE OF OPPOSING SURFACE — SPHERICAL | ○ | ○ | ○ | × |
| CYLINDRICAL | ○ | ◎ | ◎ | × |
| CONICAL | ○ | ◎ | ◎ | × |
| FLAT | ○ | ○ | ○ | × |

SET OF ARTIFICIAL TEETH HAVING CONVEX ADJUSTMENT SURFACE

BACKGROUND OF THE INVENTION

1. Field of the Invention

The present invention relates to a set of artificial teeth including at least a pair of upper and lower artificial molar teeth.

2. Description of the Related Art

With too much awareness of natural teeth, conventional artificial teeth are designed focusing on reproducing shapes of the natural teeth. In recent years, various shapes of artificial teeth have been proposed in order to produce the artificial teeth focusing on functions. Those shapes are elaborately designed so as to exert proper functions when the artificial teeth are precisely arranged.

However, even if highly functional artificial teeth can be produced at a designing stage, artificial teeth that are actually produced do not always have shapes and arrangement as designed, so that an occlusion state often becomes improper. An oral cavity is different between individual patients, and the size of the oral cavity, height and angles of residual ridges and the like vary in a clinical setting of an edentulous jaw. Thus, there is a need for advanced technique and experience for the arrangement of the artificial teeth at the time of producing a dental prosthetic appliance (plate dentures).

When the artificial teeth of the plate dentures are incompletely arranged, it is not possible to obtain an optimal occlusion state for sufficiently chewing food. Therefore, at a final stage of production of the plate dentures, an adjustment operation of scaling occlusal surfaces of the artificial teeth is performed so as to obtain a proper occlusion state. A polymerization distortion of resin for a plate or the like is caused at the time of producing the plate dentures. It is extremely difficult to predict such a distortion and arrange the artificial teeth in maxillary and mandibular arches so as to gain the arrangement, as designed, at the end. Therefore, in the conventional artificial teeth, even when the artificial teeth are arranged as carefully as possible in the production of the plate dentures, the adjustment operation of scaling the occlusal surfaces is inevitable in the end.

In a case where there are still remaining teeth or the like, it is more difficult to arrange the artificial teeth at optimal positions. Therefore, the artificial teeth often have to be displaced from the optimal positions. In this case, there is a need for a great deal of occlusion adjustment after producing the dental prosthetic appliance.

For example, Japanese Unexamined Patent Publication No. 8-280713 describes shapes of upper and lower artificial teeth and a relationship between those teeth. However, the invention of Japanese Unexamined Patent Publication No. 8-280713 is premised on an assumption that the artificial teeth are precisely arranged, and does not refer to adjustment of the occlusal surfaces in a case where the artificial teeth are not precisely arranged.

SUMMARY OF THE INVENTION

In view of the above-mentioned problems, an object of the present invention is to provide a set of artificial teeth capable of easily performing occlusion adjustment without high precision in arrangement.

In order to achieve the above object, a set of artificial teeth according to the present invention includes at least a pair of occluding upper and lower artificial molar teeth, in which one of the pair of artificial molar teeth has a convex adjustment surface which is formed of a spherical surface, a cylindrical surface or a conical surface on an occlusal surface thereof, and the other of the pair of artificial molar teeth has an opposing surface which is in point contact or line contact with the adjustment surface on an occlusal surface thereof.

With this configuration, since a contact area between the adjustment surface and the opposing surface is small, it is possible to largely change an occlusion state by slightly scaling contact parts between the adjustment surface and the opposing surface. Therefore, even when arrangement of the artificial teeth is displaced from optimal positions, it is possible to perform adjustment so as to obtain a suitable occlusion state only by slightly scaling the adjustment surface or the opposing surface.

Further, in the set of artificial teeth of the present invention, the opposing surface maybe formed of a flat surface, a spherical surface, a cylindrical surface or a conical surface, and the opposing surface is preferably convex.

With this configuration, the adjustment surface is not in surface contact but surely in point contact or line contact with the opposing surface. Further, with the convex opposing surface, a distance between the adjustment surface and the opposing surface is increased only by slightly bringing the adjustment surface and the opposing surface apart from the contact points between the surfaces. Thus, it is possible to largely change the occlusion state by slightly scaling the vicinity of the contact points.

Further, in the set of artificial teeth of the present invention, the adjustment surface and the opposing surface may be formed of a cylindrical surface or a conical surface, and straight lines including contact points on the adjustment surface and the opposing surface may be inclined by 30° to 90° relative to each other.

With this configuration, the adjustment surface comes into contact with the opposing surface at one point, and the occlusion state can be largely changed even with a small scaling amount. Therefore, even when the arrangement of the artificial teeth is displaced from designed positions, it is possible to obtain a favorable occlusion state by a slight adjustment operation.

Further, in the set of artificial teeth of the present invention, the pair of artificial molar teeth having the adjustment surface and the opposing surface may include a pair of maxillary and mandibular first molar teeth, a pair of maxillary and mandibular second molar teeth, a pair of maxillary and mandibular first premolar teeth, and a pair of maxillary and mandibular second premolar teeth.

With this configuration, it is possible to produce a dental prosthetic appliance alternative for all the molar teeth.

According to the present invention, the convex adjustment surface which is formed of a spherical surface, a cylindrical surface or a conical surface is formed on the occlusal surface of one of the pair of artificial molar teeth, and the opposing surface which is in point contact or line contact with the adjustment surface is formed on the occlusal surface of the other of the pair of artificial molar teeth. Thus, the contact area between the adjustment surface and the opposing surface is small, and it is possible to improve the occlusion state by only slightly scaling the adjustment surface or the opposing surface. Therefore, it is possible to easily correct faulty occlusion resulting from displacement of the artificial molar teeth due to a distortion at the time of producing the dental prosthetic appliance.

BRIEF DESCRIPTION OF THE DRAWINGS

These and other objects and features of the present invention will become apparent from the following description taken in conjunction with the preferred embodiments thereof with reference to the accompanying drawings, in which:

FIG. 7 is a table showing combinations of shapes applicable to the adjustment surface and the opposing surface according to the present invention.

DESCRIPTION OF THE PREFERRED EMBODIMENTS

Figure 1:
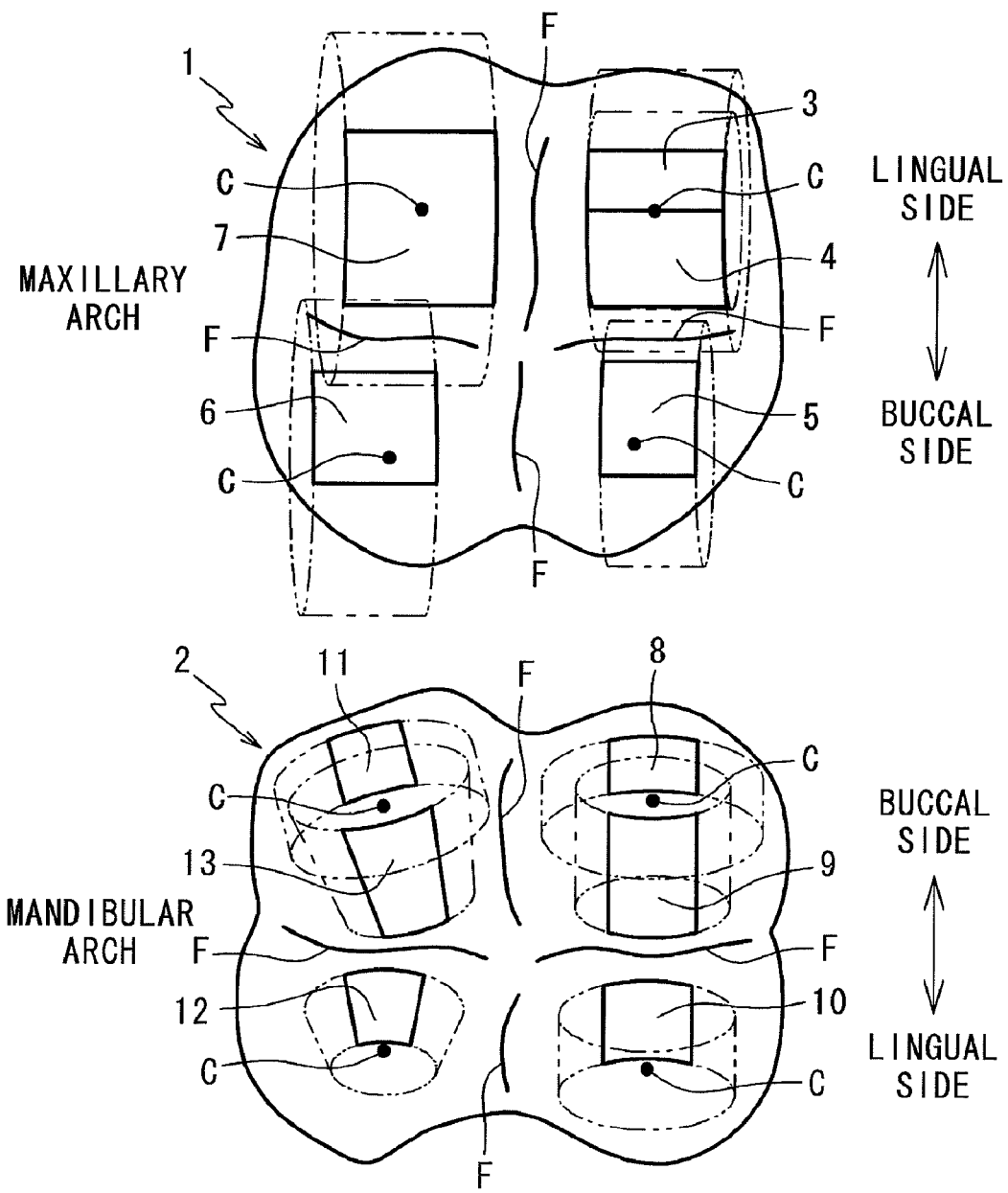
FIG. 1 is a view showing occlusal surfaces of a set of artificial teeth according to one embodiment of the present invention.

FIG. 1 shows occlusal surfaces of a set of artificial teeth according the embodiment of the present invention. This set of artificial teeth includes artificial maxillary and mandibular second molar teeth 1 and 2 that occlude with each other.

The artificial maxillary molar tooth 1 has convex cylindrical surfaces 3, 4, 5, 6 and 7 including four cusps C. The cylindrical surfaces 3, 4, 5, 6 and 7 serve as part of outer surfaces of cylinders (shown by double dotted lines) having axes which extend in a substantially mesial direction, respectively.

Occlusal surfaces around the cylindrical surfaces 3, 4, 5, 6 and 7 are formed of free form surfaces. Although outlines of the cylindrical surfaces 3, 4, 5, 6 and 7 are shown in the figure for easy understanding, the occlusal surfaces are connected to the surrounding occlusal surfaces with gentle sloping. The outlines of the cylindrical surfaces 3, 4, 5, 6 and 7 (borders with the surrounding occlusal surfaces) are not necessarily formed by straight lines as shown in the figure.

The artificial mandibular molar tooth 2 has convex cylindrical surfaces 8, 9, 10 and 11 inclined downward in a substantially buccolingual direction respectively extending from the vicinity of the cusps C toward a buccal surface or the vicinity of a fossa F, and convex conical surfaces 12 and 13 inclined downward in the substantially buccolingual direction respectively extending from the vicinity of the cusps C toward the vicinity of the fossa F. The cylindrical surfaces 8, 9, 10 and 11 and the conical surfaces 12 and 13 are also connected to surrounding occlusal surfaces which are formed of free form surfaces with gentle sloping.

Figure 2:
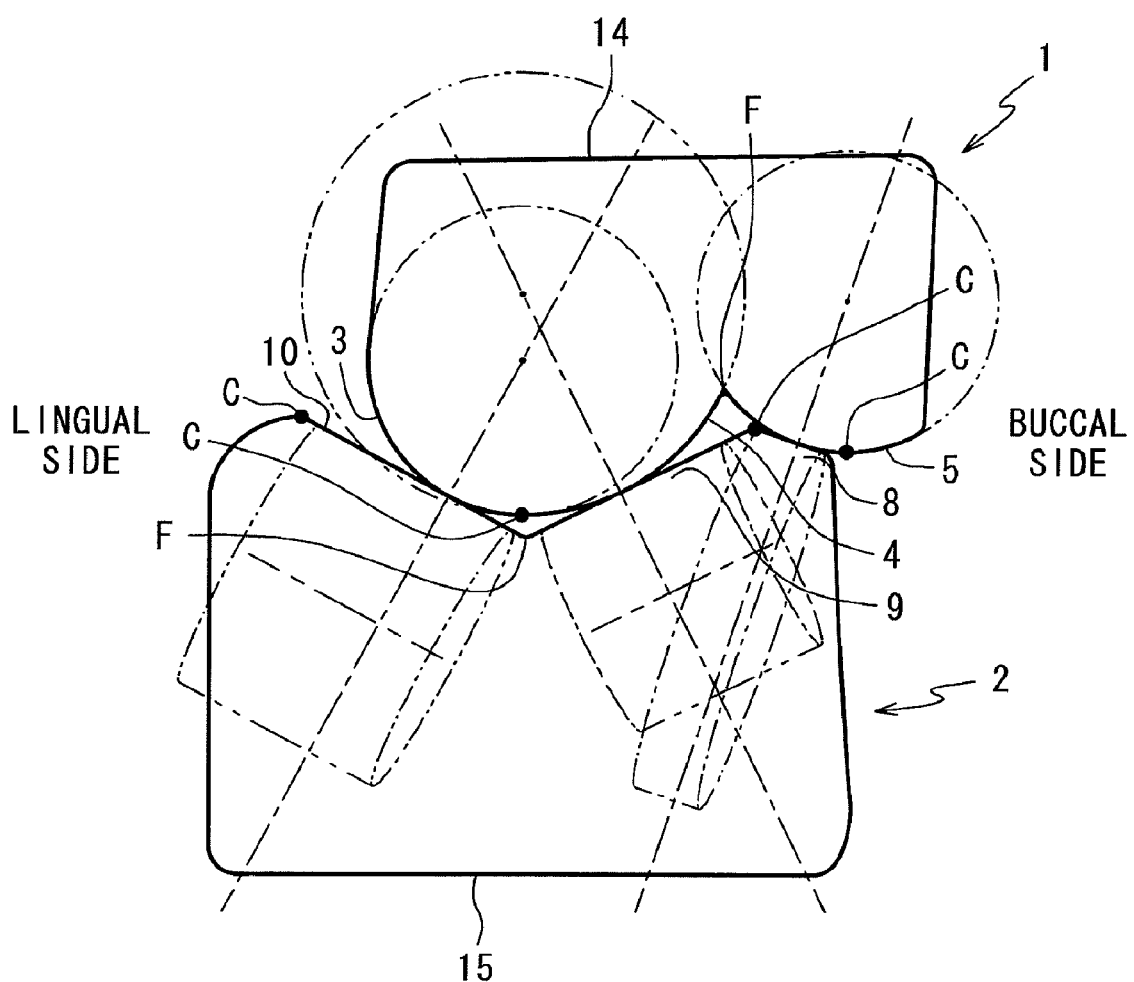
FIG. 2 is a sectional view by a plane orthogonal to a mesial-distal direction of the set of artificial teeth in FIG. 1.

FIG. 2 shows sections of the occluding artificial molar teeth 1 and 2 at occlusion positions of the cusps C on a distal side seen from the distal side. As shown in the figure, with regard to the artificial molar tooth 1 and the artificial molar tooth 2, the cylindrical surface 3, the cylindrical surface 4 and the cylindrical surface 5 are abutted with the cylindrical surface 10, the cylindrical surface 9 and the cylindrical surface 8, respectively. Although not shown in the figure, similarly, the cylindrical surface 6 is abutted with the cylindrical surface 11, and the cylindrical surface 7 is abutted with the conical surface 12 and the conical surface 13.

In the present embodiment, the cylindrical surfaces 8, 9, 10 and 11 and the conical surfaces 12 and 13 of the artificial mandibular molar tooth 2 serve as adjustment surfaces that can be scaled for occlusion adjustment, and the cylindrical surfaces 3, 4, 5, 6 and 7 of the artificial maxillary molar tooth 1 serve as opposing surfaces that comes in contact with the adjustment surfaces. However, the adjustment surfaces and the opposing surfaces are called such only relatively. In the present embodiment, the opposing surfaces 3, 4, 5, 6 and 7 may be scaled for the occlusion adjustment, or both the adjustment surfaces 8, 9, 10, 11, 12 and 13 and the opposing surfaces 3, 4, 5, 6 and 7 maybe scaled for the occlusion adjustment.

Figure 3:
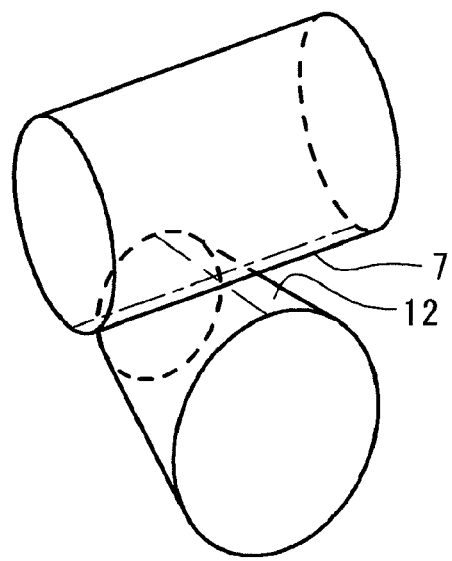
FIG. 3 is a schematic perspective view showing an adjustment surface and an opposing surface of the set of artificial teeth in FIG. 1.

FIG. 3 shows an abutment state between the cylindrical surface 7 and the conical surface 12 as a representative of these surfaces for easy understanding. The cylindrical surface 7 and the conical surface 12 having skew axes come into contact with each other at one points on respective surfaces. As shown by chain lines, one straight line including contact points (i.e., a straight meridian line can be drawn on the respective surfaces.

In a case where a posture of the artificial molar tooth 1 or the artificial molar tooth 2 is slightly inclined, for example in a case where the artificial molar tooth 1 or the artificial molar tooth 2 is inclined and fixed to a denture plate of a dental prosthetic appliance (plate dentures), not all the opposing surfaces 3, 4, 5, 6 and 7 can be abutted with the adjustment surfaces 8, 9, 10, 11, 12 and 13 as they are left unadjusted.

Figure 4:
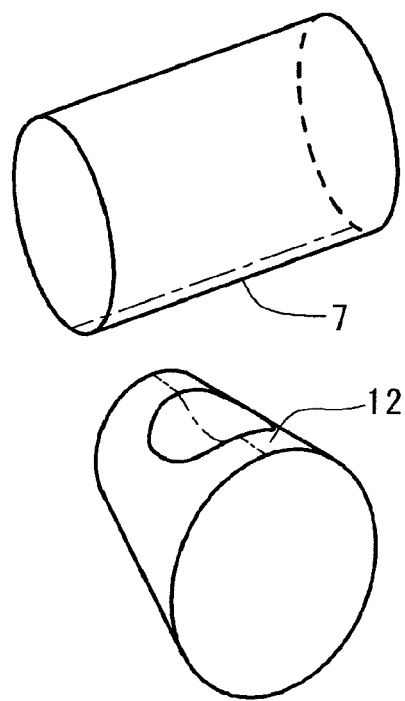
FIG. 4 is a schematic perspective view showing the adjustment surface and the opposing surface in FIG. 3 in which occlusion is corrected.
Figure 5:
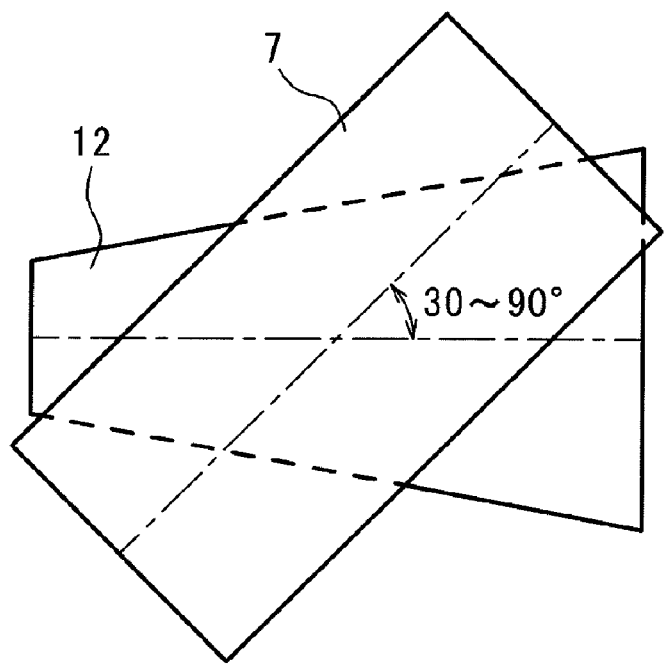
FIG. 5 is a schematic plan view showing a relationship between the adjustment surface and the opposing surface in FIG. 2.

For example, with the unadjusted dental prosthetic appliance, in a case where the cylindrical surface 7 is first abutted with the conical surface 12 so as not to obtain a proper occlusion state, the artificial molar tooth 1 and the artificial molar tooth 2 can deeply occlude by scaling an abutment part of the conical surface 12 as shown in FIG. 4. Thus, the other opposing surfaces 3, 4, 5 and 6 can be abutted with the adjustment surfaces 8, 9, 10, 11 and 13.

In this manner, it is possible to obtain an optimal occlusion state between the artificial molar tooth 1 and the artificial molar tooth 2 by scaling part of the adjustment surfaces 8, 9, 10, 11, 12 and 13 so that all the opposing surfaces 3, 4, 5, 6 and 7 come into contact with the adjustment surfaces 8, 9, 10, 11, 12 and 13.

Further, in the present embodiment, as shown in FIG. 2, the set is designed so that normal lines (shown by chain lines) at respective contact points between the adjustment surfaces 8, 9, 10, 11, 12 and 13 and the opposing surfaces 3, 4, 5, 6 and 7 pass through bottom surfaces 14 and 15 of the artificial molar tooth 1 and the artificial molar tooth 2. Thereby, at the time of occlusion of the dental prosthetic appliance using the artificial molar teeth 1 and 2, forces on the individual contact points all act in a direction of pressing the bottom surfaces 14 and 15 toward the denture plate. Therefore, the artificial molar teeth 1 and 2 are stably held on the denture plate.

As shown in FIG. 4, since the cylindrical surface 7 and the conical surface 12 have small contact areas, a distance between the axes of both the surfaces is largely reduced only by slightly scaling one of the surfaces. When an angle made between two straight lines including the contact points on faces of the cylindrical surface 7 and the conical surface 12 is reduced, areas in which the cylindrical surface 7 and the conical surface 12 overlap with each other are increased. Thus, the volume of the cylindrical surface 7 and the conical surface 12 to be scaled for reducing the distance between the axes by a fixed distance is increased. Therefore, the angle made between the two straight lines including the contact points on the faces of the cylindrical surface 7 and the conical surface 12 is preferably 30° or more, most preferably 90°.

Figure 6:
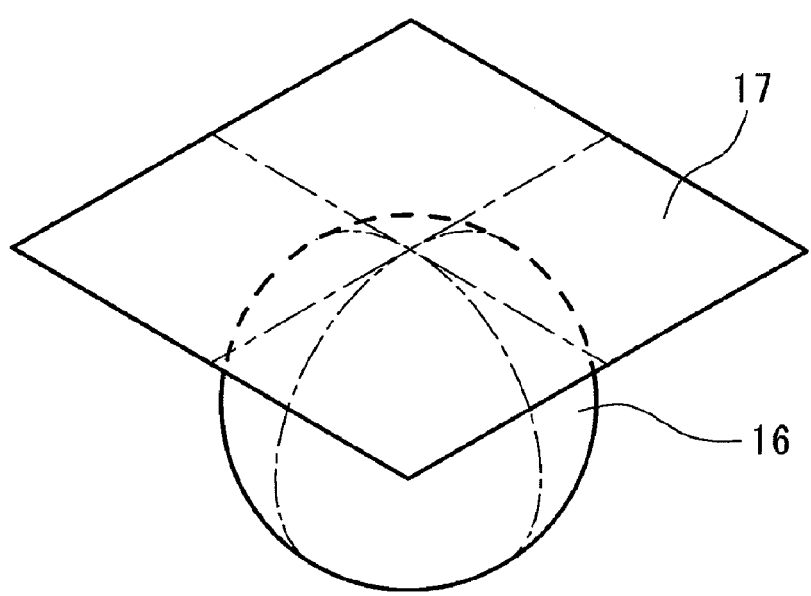
FIG. 6 is a schematic perspective view showing an alternative for the adjustment surface and the opposing surface according to the present invention.

Alternatively, as shown in FIG. 6, the adjustment surface to be scaled for the occlusion adjustment may be a spherical surface 16, and the opposing surface may be a flat surface 17. In a case where the flat surface 17 is scaled for the occlusion adjustment, a large region has to be scaled in order to form a large concave portion for receiving the spherical surface 16. Thus, the flat surface 16 is not suitable as the adjustment surface to be scaled for the occlusion adjustment.

FIG. 7 shows combinations of shapes applicable to the adjustment surface and the opposing surface of the artificial molar tooth according to the present invention. In the present invention, a cylindrical surface or a conical surface is most preferably applied to the adjustment surface and the opposing surface. When a positional relationship between a cylindrical surface or a conical surface and another cylindrical surface or another conical surface in a skew relationship is displaced, positions which are different from designed abutment points come close to each other, so as to reduce a distance between the surfaces. Thus, the surfaces can be brought into contact with each other by slightly changing a relative distance.

A cylindrical surface or a conical surface is in line contact with a flat surface, and a cylindrical surface or a conical surface can be arranged so as to be in line contact with another cylindrical surface or another conical surface. Since the occlusion adjustment is also performed only by scaling a smaller region than a case of wide surface contact in this case, the combinations of the shapes above can be adopted in the present invention.

Spherical surfaces can be adopted as the adjustment surface and the opposing surface. However, in a case where relative positions of the spherical surfaces are displaced, the distance between the surfaces is easily increased. Thus, there is a need for increasing an amount of scaling other adjustment surfaces.

Further, in the present invention, a functional cusp of the artificial molar tooth is preferably provided with three or more adjustment surfaces or opposing surfaces. The functional cusp is abutted with a plurality of cusps of the occluding artificial molar tooth. Thus, by providing the adjustment surfaces or the opposing surfaces of the present invention at abutment positions of the cusps, it is possible to easily perform the occlusion adjustment of the dental prosthetic appliance.

Moreover, in the present invention, when a straight line passing through the designed contact point of the opposing surface is matched with a sliding direction of the artificial molar tooth, sliding of the artificial molar tooth is guided by sliding contact between the adjustment surface and the opposing surface so as to exert a stable grinding function. In this case, the opposing surface for guiding the sliding is better not scaled but only the adjustment surface is scaled.

Further, in the artificial molar tooth of the present invention, a shortest route extending from the vicinity of the cusp to the fossa or parts in peripheral edges preferably includes one adjustment surface or opposing surface, and also preferably has no inflection point provided over an area from the cusp to the fossa or the peripheral edges.

Further, the set of artificial teeth of the present invention preferably includes a pair of artificial maxillary and mandibular first molar teeth, a pair of artificial maxillary and mandibular second molar teeth, a pair of artificial maxillary and mandibular first premolar teeth, and a pair of artificial maxillary and mandibular second premolar teeth, respectively provided with the adjustment surfaces and the opposing surfaces described above.

Further, the set of artificial teeth of the present invention may include artificial molar teeth having conventional occlusion shapes, and further include a pair of canines and artificial incisors.

The set of artificial teeth of the present invention is utilized for producing the dental prosthetic appliance.

What is claimed is:

1. A set of artificial teeth comprising:
   at least one pair of occluding upper and lower artificial molar teeth, wherein
   one of the pair of artificial molar teeth has an occlusal surface with a plurality of convex adjustment surfaces that are scalable for occlusal adjustment formed thereon, each of the convex adjustment surfaces being formed as a cylindrical surface or a conical surface and having a straight meridian line,
   another of the pair of artificial molar teeth has an occlusal surface with a plurality of opposing surfaces formed thereon, each of the opposing surfaces being formed as a cylindrical surface or a conical surface and having a straight meridian line,
   each of the convex adjustment surfaces has only one point of contact with one of the opposing surfaces along their respective straight meridian lines,
   a longitudinal center axis of the cylindrical surface or the conical surface forming each of the convex adjustment surfaces and a longitudinal center axis of the cylindrical surface or the conical surface forming the one of the opposing surfaces are not parallel to each other, and
   each of the convex adjustment surfaces at the one point of contact is scalable such that after scaling all of the opposing surfaces contact the convex adjustment surfaces.

2. The set of artificial teeth according to claim 1, wherein the straight meridian line of each of the convex adjustment surfaces is angled by 30° to 90° with respect to the straight meridian line of the one of the opposing surfaces.

3. The set of artificial teeth according to claim 1, wherein the at least one pair of artificial molar teeth having the convex adjustment surfaces and the opposing surfaces includes a pair of maxillary and mandibular first molar teeth, a pair of maxillary and mandibular second molar teeth, a pair of maxillary and mandibular first premolar teeth, and a pair of maxillary and mandibular second premolar teeth.

4. The set of artificial teeth according to claim 2, wherein the at least one pair of artificial molar teeth having the convex adjustment surfaces and the opposing surfaces includes a pair of maxillary and mandibular first molar teeth, a pair of maxillary and mandibular second molar teeth, a pair of maxillary and mandibular first premolar teeth, and a pair of maxillary and mandibular second premolar teeth.

* * * * *